United States Patent [19]

Burger et al.

[11] Patent Number: 4,820,835

[45] Date of Patent: Apr. 11, 1989

[54] RADIOLABELED BENZAZEPINE

[75] Inventors: Walter Burger, Midland Park; Arnold A. Liebman, Verona, both of N.J.; Clark W. Perry, Danbury, Conn.

[73] Assignee: Hoffmann-La Roche Inc., Nutley, N.J.

[21] Appl. No.: 880,228

[22] Filed: Jun. 30, 1986

[51] Int. Cl.$^4$ .................. C07D 121/70; C07D 487/04; C07D 207/34

[52] U.S. Cl. .................... 540/577; 548/561; 558/701

[58] Field of Search .................. 558/401; 548/561; 540/577

[56] References Cited

U.S. PATENT DOCUMENTS 4,239,744 12/1980 Paul et al. .................. 424/1
4,436,662 3/1984 Fryer et al. .................. 548/461 X

OTHER PUBLICATIONS

Abstracts, Society for Neuroscience, vol. 10, Oct. 10-15, 1984.
Eu. Journal of Pharmacology, 113 (Jul. 11, 1985) 147-148.
Proc. Nat. Acad. Sci. (U.S.A.) 77, pp. 1666-1670, (1980).

Primary Examiner—Richard L. Raymond
Assistant Examiner—W. B. Springer
Attorney, Agent, or Firm—Jon S. Saxe; Bernard S. Leon; Matthew Boxer

[57] ABSTRACT

A compound of the formula:

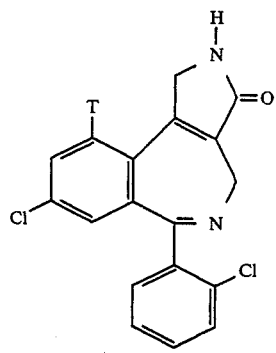

wherein T is tritium;

is described as well as intermediates for its preparation. The compound of formula I is useful in an assay for detecting the presence of benzodiazepine receptor occupiers in a warmblooded animal.

5 Claims, 2 Drawing Sheets

RADIOLABELED BENZAZEPINE

BRIEF SUMMARY OF THE INVENTION

The present invention relates to intermediates in the preparation of a radiolabeled benzazepine which is useful in an assay for detecting the presence in a warmblooded animal of a benzodiazepine or other compound which interacts with the central nervous system (CNS) benzodiazepine receptor and which is also useful in an assay of test compounds for benzodiazepine-like agonist, antagonist or mixed agonist/antagonist properties. The invention also relates to the radiolabeled benzazepine itself.

DETAILED DESCRIPTION OF THE INVENTION

Figure 1:
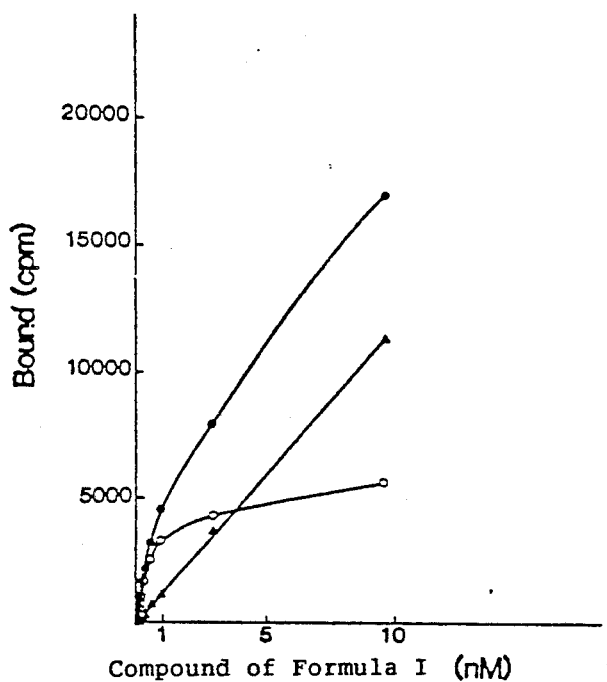
Figure 2:
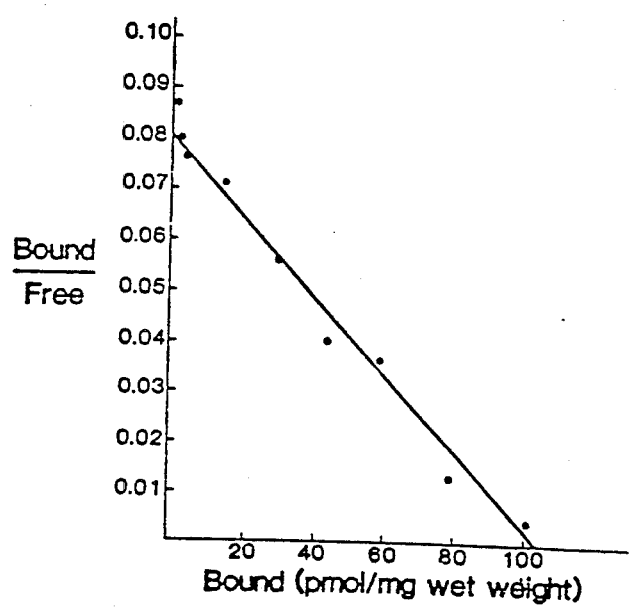

As used herein the symbol "$^3H$" and also the symbol "t" denote a tritium atom.

As used herein the term "benzodiazepine-like activity" denotes the minor tranquilizing activity of benzodiazepines such as, for example, sedation, muscle-relaxation, and anti-anxiety activity.

The radiolabeled benzazepine of the invention is a compound of the formula:

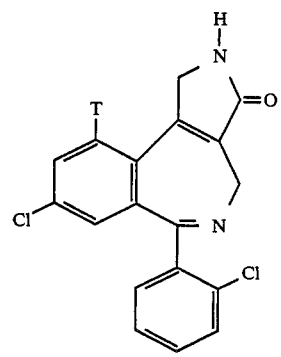

wherein T is a tritium atom.

The compound of formula I may be prepared by the following formula scheme:

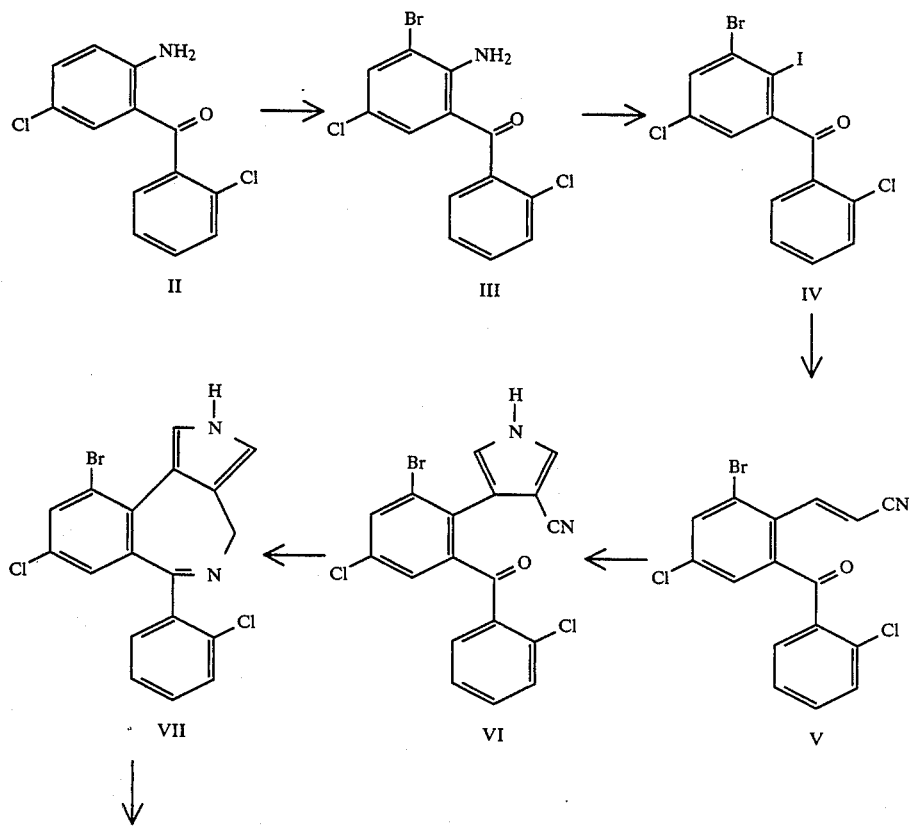

-continued

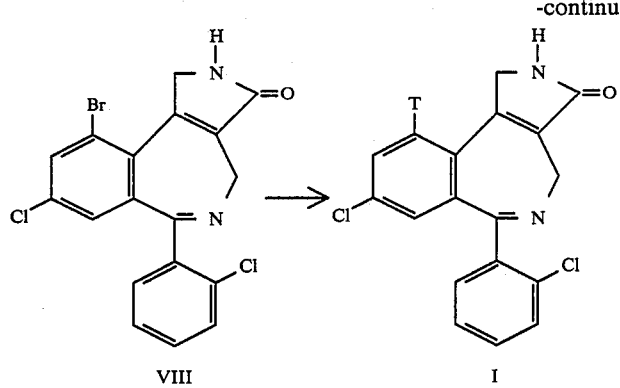

VIII       I wherein T is a tritium atom.

As illustrated in the formula scheme, the compound of formula II, which can be prepared according to known methods, is converted to the compound of formula III by treatment with bromine. The reaction is conducted at reflux in a polar organic solvent such as chloroform, or more preferably acetic acid. The compound of formula III is recovered by conventional means such as crystallization from a lower alkanol such as propanol, methanol or more preferably ethanol.

The compound of formula III is converted to the compound of formula IV by treatment with nitrosylsulfuric acid and sulfuric acid at a temperature in a range of about 40° C. to about 50° C., more preferably at about 45° C., addition of ice water, and further treatment with sodium tetrafluoroborate. The resulting tetrafluoroborate salt is mixed with a solution of water and ethyl acetate and treated with an alkali metal iodide such as potassium iodide. The resulting mixture is extracted and treated with an agent such as sodium tetrathionate or more preferably sodium thiosulfate to remove excess iodide. The resulting compound of formula IV is recovered by conventional means such as crystallization.

The compound of formula IV is converted to the compound of formula V by treatment with triphenylphosphine and acrylonitrile in a polar organic solvent such as pyridine or more preferably a 5:1 mixture by volume of acetonitrile and triethylamine, at reflux under an inert atmosphere such as argon or nitrogen. Palladium diacetate is added and heating is continued. The resulting compound of formula V is recovered by conventional means such as chromatography followed by crystallization.

The compound of formula V is converted to the compound of formula VI by treatment at about room temperature, for example about 20° C. to about 25° C., with p-toluene-sulfonylmethyl isocyanide in a polar aprotic solvent, such as dimethylformamide or more preferably dimethylsulfoxide, and ether; followed by treatment with an alkali metal hydride such as calcium hydride, potassium hydride, or more preferably sodium hydride. The resulting reaction mixture is diluted with water and the compound of formula VI is recovered by conventional means such as extraction, followed by chromatography and then recrystallization.

The compound of formula VI is converted to the compound of formula VII by treatment at about room temperature, under a hydrogen atmosphere, with Raney nickel. The compound of formula VII is recovered by conventional means such as chromatography followed by crystallization.

The compound of formula VII is converted to the compound of formula VIII by reaction at about room temperature with an oxidizing agent like a "peracid" such as hydrogen peroxide, perbenzoic acid, or more preferably m-chloroperbenzoic acid, followed by treatment with an excess of a reducing agent such as sodium sulfite. The compound of formula VIII is recovered by conventional means such as extraction, followed by chromatography an then crystallization.

The compound of formula VIII is converted to the compound of formula I by treatment with Lindlar catalyst suspended in tetrahydrofuran and triethylamine, followed by introduction of tritium gas, for example, by a Toeppler pump. After removal of unreacted tritium gas, for example, also by Toeppler pump, the resulting compound of formula I is recovered by conventional means such as crystallization, followed by chromatography and recrystallization.

The compound of formula I is useful as an agent in a radioreceptor assay for measuring compounds in a biological specimen such as plasma, body fluids, or tissue samples of a warmblooded animal which would occupy benzodiazepine receptor sites.

Specifically, the compound of formula I is useful as an agent for screening whether a test compound has the ability to occupy or bind to CNS benzodiazepine receptor sites. The terms "occupy" or "bind to" a receptor site are used synonymously in the specification.

More specifically, the compound of formula I binds to CNS benzodiazepine receptor sites. The degree to which a test compound will displace the compound of formula I from CNS benzodiazepine receptor sites shows the test compound's ability as either an agonist, antagonist or mixed agonist/antagonist of benzodiazepine-like activity. Further testing which is beyond the scope of the invention and which is conventional would be needed to determine whether a particular test compound which binds to CNS benzodiazepine receptors is an agonist, antagonist or mixed agonist/antagonist of benzodiazepine-like activity.

As used herein the term "agonist" denotes ability to initiate or promote a particular drug activity. The term "antagonist" denotes the ability to block a particular drug activity.

An advantage of the compound of formula I as compared to almost all known ligands for benzodiazepine receptors, is that the compound of formula I gives a high level of specific binding at physiologic temperatures (about 37° C.). Accordingly, and most preferably, the compound of formula I is useful as an agent for assaying in vivo binding of test compounds, which are also referred to herein as benzodiazepine receptor occupiers, to CNS benzodiazepine receptor sites.

For example, the compound of formula I is injected into a warmblooded animal. At a suitable time thereafter, for example 10-30 minutes, the warm-blooded animal is injected with the test compound. At a suitable time thereafter, for example 10-30 minutes, the warm-blooded animal is sacrificed, the brains are removed, and radioactivity is measured by standard counting methods. The lower the radioactivity, for example, the greater the degree to which the test compound has displaced the compound of formula I. Alternatively, in in vivo testing the order of injection of the compound of formula I and the test compound can be reversed.

The compound of formula I has a high specific radioactivity. The specific radioactivity of the compound of formula I can be as high as about 22 Ci/mmol.

The higher the specific radioactivity of a compound, the greater is its sensitivity in measuring biological activity.

Because the compound of formula I has a high specific radioactivity, and also has a high binding affinity for the CNS benzodiazepine receptor, the compound of formula I is useful for assaying in vivo binding as described above. Specifically, the compound of formula I is useful in an in vivo assay, as described above, for detecting both the presence and the concentration of test compound.

The compound of formula I is also useful for in vitro monitoring of CNS benzodiazepine-receptor occupiers in plasma or another biological specimen in a radioreceptor assay. Specifically, the compound of formula I is useful in an in vitro assay, for detecting both the presence and the concentration of test compound.

An in vitro method for detecting the concentration of a benzodiazepine contained in a biological specimen from a warm-blooded animal wherein the biological specimen is selected from the group consisting of blood plasma, urine, cerebral spinal fluid, and saliva comprises:

(a) treating the biological specimen to precipitate a protein therefrom, and leave a protein-free remainder, (b) separating the protein-free remainder of the biological specimen, (c) mixing a suspension of synaptosomal membranes with the protein-free remainder, (d) adding 8-chloro-6-(2-chlorophenyl)-1,4-dihydropyrrolo[3,4-d][2]-10-t-benzazepin-3(2H)-one (the compound of formula I) to the mixture obtained in step (c), (e) incubating the radioactive mixture obtained in step (d), (f) filtering or otherwise separating the incubate from step (e) to obtain a mass comprising the said synaptosomal membranes, and 8-chloro-6-(2-chlorophenyl)-1,4-dihydropyrrolo[3,4-d][2]-10-t-benzazepin-3(2H)-one bound thereto, (g) measuring the radiation of the mass of step (f).

Among the compounds which thus can be measured include diazepam, flurazepam, chlordiazepoxide and the like.

Methods for detecting the concentration of a benzodiazepine in a biological specimen from a warm-blooded animal are known in the literature, for example, as set forth in U.S. Pat. No. 4,239,744 the contents of which are incorporated herein by reference.

The following standard test procedures demonstrate the utility of the compound of formula I. Compound of formula I with a radioactivity of 22Ci/mmol was used in in vitro studies of benzodiazepine (BZ) receptor binding which were conducted as follows. Cerebral cortical tissue from rats (male, 180 g, Sprague-Dawley, Hilltop Farms) was made homogeneous, washed 5 times and incubated for 60 minutes with the compound of formula I in 5 ml of buffer (50 mM Tris-HCl, pH 7.7) at a final tissue concentration of 0.5 mg/ml original wet weight. Clonazepam at a concentration of $10^{-6}$M was used in a determination of nonspecific binding. Assays were ended by filtration. Radioactivity was determined using standard liquid scintillation counting methods. The following results were obtained for the compound of formula I

| $K_d$ (nM) | $B_{max}$ (mol/mg wet weight) | Ratio (Specific/nonspecific) | Temp °C. |
|---|---|---|---|
| 0.18 ± 0.05 nM | 1.36 × $10^{-10}$ | 12 | 0 |
| 0.82 ± 0.03 nM | 1.22 × $10^{-10}$ | 4 | 37 |

The specific/nonspecific binding ratio is taken when the concentration of the compound of formula I is at $K_d$. The amount of specific binding is determined by subtracting the amount of nonspecific binding from the total binding. Ethyl-8-fluoro-5,6-dehydro-5-methyl-6-oxo-4H-imidazol-[1,5-a]-1,4[benzodiazepine-3-carboxylate] (benzodiazepine antagonist), midazolam and clonazepam (benzodiazepine agonists) prevented the binding of the compound of formula I with $K_i$ values in the nM range, while compounds preferring peripheral benzodiazepine sites did not.

The in vitro saturation of the compound of formula I binding at 37° C. is shown in FIG. 1. In FIG. 1, ● is total binding; ▌ is non-specific binding; o is specific binding. FIG. 1 represents a test with rat cerebral cortical tissue as described above. The concentrations of the compound of formula I, were from 0.01 to 10 nM. The plots in FIG. 1 are from a representative test. With incubations at physiologic temperatures specific to nonspecific ratios were high over a relatively large range of concentrations.

In vivo binding of the compound of formula I was determined according to the following procedures. Mice (male, 30 g ICR, Hilltop Farms) were injected via the tail vein with the compound of formula I. Ten or 30 minutes later, the mice were killed, the cerebral cortices of the brains were dissected, solubilized, and the radioactivity was determined using standard methods. In order to determine nonspecific binding, some mice were pretreated with 5 mg/kg clonazepam (30 min ip). Specific/nonspecific binding ratios in cerebral cortex were about 2 at 10 minutes. The tissues in these tests were assayed directly without first homogenizing and washing them to reduce nonspecific binding. Therefore, the ratios were true in vivo ratios. Radioactivity was low and specific binding was negligible at 30 minutes.

The data given show that the compound of formula I has a high affinity and is a selective ligand for BZ receptors in the brain. The compound of formula I has useful specific/nonspecific ratios in vitro and in vivo at 37° C. Therefore, this compound, at physiologic temperatures and conditions, is a most useful BZ receptor agonist ligand.

The following examples further illustrate the invention.

EXAMPLE 1

(2-Amino-3-bromo-5-chlorophenyl)(2-chlorophenyl)-methanone (the compound of formula III)

A 20 g sample of (2-amino-5-chlorophenyl)(2-chlorophenyl)methanone, (the compound of formula II) a compound which can be prepared according to known methods, was dissolved in 100 mL of acetic acid and 4 mL of bromine was added. The mixture was heated at reflux for two hours, cooled and concentrated in vacuo to a residue which was crystallized from ethanol yielding (2-amino-3-bromo-5-chlorophenyl)(2-chlorophenyl)-methanone having a m.p. of 100°–101° C.

EXAMPLE 2

(3-Bromo-5-chloro-2-iodophenyl)(2-chlorophenyl)-methanone (the compound of formula IV)

An 11.4 g sample of the product of Example 1 (33 mmol) was added portionwise with stirring to a mixture of 36.5 mmol of 40% nitrosylsulfuric acid and 9 mL of concentrated sulfuric acid. The rate of addition was such that the internal temperature was maintained below 45° C. After the addition was completed, stirring was maintained at room temperature for 1.5 hours when the mixture was poured into 75 mL of ice water and filtered. To the filtrate, a solution of 2.2 g of sodium tetrafluoroborate in 15 mL of water was slowly added. The resulting mixture was refrigerated overnight, filtered and the precipitate washed with 12 mL of ice water. The precipitated tetrafluoroborate salt was then stirred in a mixture of 70 mL of water and 25 mL of ethyl acetate while a solution of 11 g (66 mmol) of potassium iodide in 40 mL of water was added over a 20 minute period. The resulting mixture was extracted with three 50 mL portions of methylene chloride which were combined and in turn extracted with 25 mL of 5% sodium thiosulfate solution. The organic extract was concentrated in vacuo to a residual solid which was dissolved in ether and refrigerated overnight. Impurities (mainly bromo-dichlorofluorenone, m.p. 183°–184° C.) were removed by filtration and the filtrate crystallized by concentration to the product which was then recrystallized from ether to produce (3-bromo-5-chloro-2-iodophenyl)(2-chlorophenyl)-methanone having a m.p. of 86°–87° C.

EXAMPLE 3

(E)-3-[2-Bromo-4-chloro-6-(2-chlorobenzoyl)]-2-propenenitrile (The compound of formula V)

A solution of the end product of Example 2 (1.61 g, 3.66 mmol), triphenylphosphine (100 mg), acrylonitrile (5 mL), acetonitrile (5 mL), and triethylamine (1 mL) was stirred at room temperature under nitrogen for 5 minutes then it was heated to gentle reflux. Palladium diacetate (325 mg) was added portionwise over a period of 2 hours and heating was continued for an additional 6 hours. After cooling, the mixture was filtered and the filtrate concentrated under reduced pressure to a residue which was chromatographed over silica gel (E. Merck, Silica Gel 60, 50 g). Elution with chloroform gave the product as light tan crystals. Crystallization of part of this from a mixture of ether, chloroform and petroleum ether yielded pure (E)-3-[2-Bromo-4-chloro-6-(2-chlorobenzoyl)]-2-propenenitrile m.p. 120°–121° C.

EXAMPLE 4

4-[2-Bromo-4-chloro-6-(2-chlorobenzoyl)]-1H-pyrrole-3-carbonitrile (the compound of formula VI)

A mixture of the end product of Example 3 obtained above, 275 mg (0.72 mmol) and 0.75 mmol of p-toluenesulfonylmethyl isocyanide ("TosMIC") in 2 mL of dimethyl sulfoxide and 4 mL of ether was added dropwise to a stirred mixture of sodium hydride (1.5 mmol) and 3 mL of ether at room temperature. Stirring was continued for an additional 2 hours, then the reaction mixture was diluted with water and extracted with ether to obtain the crude product which was purified by chromatography on a column of silica gel. Elution with methylene chloride, concentration of the appropriate fractions and crystallization of the residue afforded pure 4-[2-bromo-4-chloro-6-(2-chlorobenzoyl)]-1H-pyrrole-3-carbonitrile with m.p. of 203°–204° C.

EXAMPLE 5

10-Bromo-8-chloro-6-(2-chlorophenyl)-2,4-dihydropyrrolo[3,4-d][2]benzazepine (the compound of formula VII)

The cyanopyrrole of Example 4 obtained above, 110 mg (0.26 mmol), was stirred for 5 h at room temperature under an atmosphere of hydrogen in the presence of fresh Raney nickel catalyst (300 mg, washed with acetic acid) in 4 mL of acetic acid and 1 mL of THF. After filtration of the catalyst, the solution was concentrated, partitioned between dilute aqueous ammonium hydroxide and ether and the residue obtained from the ether layer was chromatographed on a column of silica gel. Elution with ethyl acetate-dichloromethane (1:1), concentration of the appropriate fractions and crystallization of the residue from ether-petroleum ether yielded the desired 10-bromo-8-chloro-6-(2-chlorophenyl)-2,4-dihydropyrrolo[3,4-d][2]benzazepine.

EXAMPLE 6

10-Bromo-8-chloro-6-(2-chlorophenyl)-1,4-dihydropyrrolo[3,4-d][2]benzazepin-3(2H)-one (the compound of formula VIII)

A solution of the end product of Example 5, 91 mg (obtained above), and 75 mg of m-chloroperbenzoic acid in 3 mL of acetic acid containing 2% sulfuric acid was stirred for 1 hour at room temperature. Sodium sulfite, 100 mg, was added and stirring continued for 10 min. The mixture was then concentrated in vacuo and the residue partitioned between aqueous ammonium hydroxide solution and methylene chloride. The residue from the methylene chloride extract was chromatographed on a column of silica gel with ethyl acetate elution. Concentration of the appropriate fractions and crystallization of the residue from ether provided the desired 10-bromo-8-chloro-6-(2-chlorophenyl)-1,4-dihydropyrrolo[3,4-d][2]benzazepin-3(2H)-one with m.p. of 232° C.

EXAMPLE 7

8-Chloro-6-(2-chlorophenyl)-1,4-dihydropyrrolo-[3,4-d][2]-10-t-benzazepin-3(2H)-one (the compound of formula I)

A 10 mL round bottom flask containing a magnetic stirring bar was charged with 35 mg of Lindlar catalyst (5% Pd on $CaCO_3$ poisoned with Pb), 18 mg of the end product of Example 6 (obtained above), 1 mL of tetrahydrofuran and 0.2 mL triethylamine. The flask was fitted with an appropriate stopcock and the mixture was degassed. Carrier free tritium gas (10 Ci, 0.17 mmol) was introduced with a Toeppler pump and the reaction mixture was stirred at room temperature for 35 minutes after which time any unreacted tritium gas was transferred out of the flask. The catalyst was then removed by filtration and the filtrate partitioned between aqueous ammonium hydroxide solution and dichloromethane. Crystallization of the residue from the dichloromethane extract from dichloromethane-ether yielded crude product which was chromatographed on a silica gel column, elution being accomplished with acetonitrile. Concentration of the appropriate fractions and crystallization of the residue from dichloromethane-ether yielded pure 8-chloro-6-(2-chlorophenyl)-1,4-dihydropyrrolo-[3,4-d][2]-10-t-benzazepin-3(2H)-one 237 mCi, with specific activity of 22 Ci/mmole. Radiochemical purity was 98%.

EXAMPLE 8

A radioreceptor assay method for routinely determining the concentration of pharmacologically active benzodiazepines, their pharmacologically-active metabolites, and mixtures thereof or compounds interacting with the benzodiazepine receptor contained in a biological specimen selected from the group consisting of blood plasma, urine, cerebral spinal fluid, and saliva comprises:

(a) diluting the biological specimen with water,
(b) adding perchloric acid to the diluted biological specimen obtained in step (a) to obtain a mixture containing the protein of the biological specimen which is precipitated by said perchloric acid as well as the protein-free remainder of the biological specimen which is present as a supernatant liquid.
(c) separating the supernatant liquid containing the protein-free remainder of the biological specimen obtained in step (b) from the protein precipitate;
(d) diluting the supernatant liquid separated in step (c) with distilled water;
(e) adding at least about 1 ml of a synaptosomal membranes suspension, containing about from 0.5 to 5.0 mg of protein per ml of said synaptosomal membranes suspension, to the diluted supernatant liquid (or a portion thereof) obtained in step (d).
(f) adding 8-chloro-6-(2-chlorophenyl)-1,4-dihydropyrrolo[3,4-d][2]-10-t-benzazepin-3(2H)-one having a specific activity of about 22Ci/mmol, to the mixture containing the synaptosomal membranes and the supernatant liquid obtained in step (e);
(g) incubating the radioactive mixture obtained in step (f) at a temperature of about from 0° C. to about 40° C., for about 10 to about 90 minutes;
(h) terminating the incubation carried out in step (g) with a wash containing about 5 ml of ice-cold 50 mM Tris buffer at a pH of about 7.4;
(i) filtering or otherwise separating the incubate obtained in step (h) to obtain a mass comprising the said synaptosomal membranes and 8-chloro-6-(2-chlorophenyl)-1,4-dihydropyrrolo-[3,4-d][2]-10-t-benzazepin-3(2H)-one having a specific activity of about 22Ci/mmole, bound thereto retained in the filter;
(j) washing the filter and mass retained therein obtained in step (i) with about 5 ml of said ice-cold buffer, and drying the said filter and mass retained therein;
(k) suspending the dried filter and mass retained therein obtained in step (j) in a liquid scintillation fluor; and
(l) measuring the radiation of said mass in the fluor of step (k) with a liquid scintillation counter to determine the concentration in the biological specimen of the benzodiazepines or their pharmacologically-active metabolites or any compound, which affects or blocks benzodiazepine activity by binding to the benzodiazepine receptor.

What is claimed is:

1. A compound of the formula

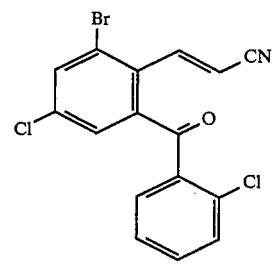

V

2. A compound of the formula

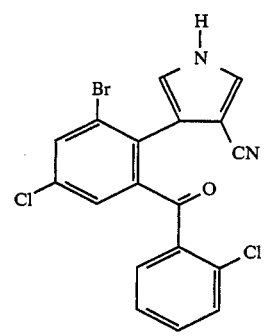

VI

3. A compound of the formula

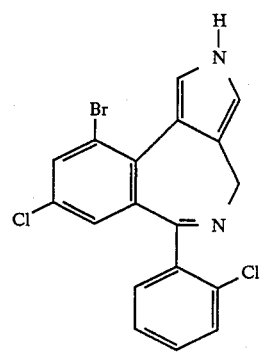

VII

4. A compound of the formula

5. A compound of the formula
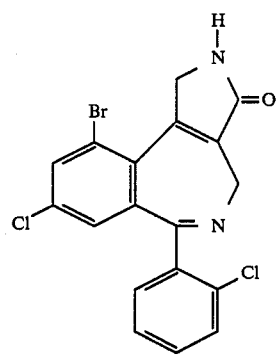
VIII
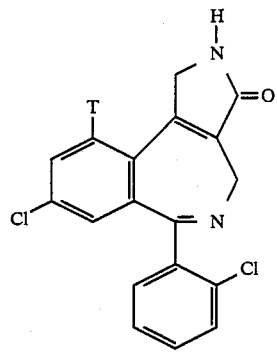
I
wherein T is a tritium atom.
* * * * *